US009512201B2

(12) United States Patent
van den Nieuwenhof et al.

(10) Patent No.: US 9,512,201 B2
(45) Date of Patent: Dec. 6, 2016

(54) HUMAN BINDING MOLECULES CAPABLE OF BINDING TO AND NEUTRALIZING HEPATITIS B VIRUSES AND USES THEREOF

(71) Applicant: Crucell Holland B.V., Leiden (NL)

(72) Inventors: Ingrid van den Nieuwenhof, Amsterdam (NL); Marijn van der Neut Kolfschoten, Amsterdam (NL); Constantin Adrian Apetri, Noordwijkerhout (NL); Robert H. E. Friesen, Leiden (NL)

(73) Assignee: Janssen Vaccines & Prevention B.V., Leiden (NL)

(*) Notice: Subject to any disclaimer, the term of this patent is extended or adjusted under 35 U.S.C. 154(b) by 70 days.

(21) Appl. No.: 14/428,904

(22) PCT Filed: Sep. 24, 2013

(86) PCT No.: PCT/EP2013/069828
§ 371 (c)(1),
(2) Date: Mar. 17, 2015

(87) PCT Pub. No.: WO2014/048910
PCT Pub. Date: Apr. 3, 2014

(65) Prior Publication Data

US 2015/0232537 A1 Aug. 20, 2015

Related U.S. Application Data

(60) Provisional application No. 61/706,518, filed on Sep. 27, 2012.

(30) Foreign Application Priority Data

Sep. 27, 2012 (EP) .................................... 12186261

(51) Int. Cl.

| | |
|---|---|
| ***A61K 39/395*** | (2006.01) |
| ***A61K 47/48*** | (2006.01) |
| ***C07K 16/46*** | (2006.01) |
| ***A61K 45/06*** | (2006.01) |
| ***C07K 16/28*** | (2006.01) |
| ***C07K 16/08*** | (2006.01) |
| ***G01N 33/569*** | (2006.01) |
| *A61K 39/00* | (2006.01) |
| *C07K 16/18* | (2006.01) |
| *C07K 16/30* | (2006.01) |

(52) U.S. Cl.
CPC ....... *C07K 16/082* (2013.01); *G01N 33/56983* (2013.01); *A61K 45/06* (2013.01); *A61K 2039/505* (2013.01); *C07K 16/18* (2013.01); *C07K 16/3007* (2013.01); *C07K 2317/56* (2013.01); *C07K 2317/565* (2013.01); *C07K 2317/76* (2013.01); *G01N 2333/02* (2013.01)

(58) Field of Classification Search
CPC .. A61K 2039/505; A61K 45/06; B82Y 5/00; C07K 16/18; C07K 16/3007
See application file for complete search history.

(56) References Cited

U.S. PATENT DOCUMENTS

| | | | |
|---|---|---|---|
| 2010/0260712 | A1 | 10/2010 | Kim et al. |
| 2011/0097270 | A1 | 4/2011 | Schofield et al. |
| 2012/0264921 | A1 | 10/2012 | Kim et al. |

FOREIGN PATENT DOCUMENTS

| | | | |
|---|---|---|---|
| WO | 8403564 | A1 | 9/1984 |
| WO | 9309872 | A1 | 5/1993 |
| WO | 9747653 | | 12/1997 |
| WO | 9747654 | | 12/1997 |
| WO | 0063403 | A2 | 10/2000 |
| WO | 2009069917 | A1 | 6/2009 |
| WO | 2014048910 | A1 | 4/2014 |

OTHER PUBLICATIONS

Eren et al., Preclinical evaluation of two human anti-hepatitis B Virus (HBV) monoclonal antibodies in the HBV-Trimera Mouse Model and in HBV Chronic Carrier Chimpanzees, Hepatology, Sep. 1, 2000, pp. 588-596, vol. 32, No. 3, Wiley, USA.
Hong et al., In vivo neutralization of hepatitis B virus infection by an anti-preS1 humanized antibody in chimpanzees, Virology, Jan. 5, 2004, pp. 134-141, vol. 318, No. 1, Elsevier, Amsterdam, NL.
Niedre-Otomere et al., Recombinant Semliki Forest virus vectors encoding hepatitis B virus small surface and pre-S1 antigens induce broadly reactive neutralizing antibodies, May 17, 2012, Biosciences Information Service, Philadelphia, PA, US.
PCT International Search Report, PCT/EP2013/069828, dated Dec. 5, 2013.
PCT International Written Opinion, PCT/EP2013/069828, dated Dec. 5, 2013.

*Primary Examiner* — Janet L Andres
*Assistant Examiner* — Barry A Chestnut
(74) *Attorney, Agent, or Firm* — TraskBritt, P.C.

(57) ABSTRACT

The disclosure relates to binding molecules, such as human monoclonal antibodies, that bind to Hepatitis B viruses, and have a broad neutralizing activity against such Hepatitis B viruses. The disclosure further provides nucleic acid molecules encoding the binding molecules, and compositions comprising the binding molecules. The binding molecules can be used in the diagnosis, prophylaxis and/or treatment of Hepatitis B.

14 Claims, 7 Drawing Sheets

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial
<220> FEATURE:
<223> OTHER INFORMATION: CR8097 VH CDR1

<400> SEQUENCE: 1

Gly Phe Thr Phe Ser Asn Asn Trp
1               5


<210> SEQ ID NO 2
<211> LENGTH: 8
<212> TYPE: PRT
<213> ORGANISM: Artificial
<220> FEATURE:
<223> OTHER INFORMATION: CR8097 VH CDR2

<400> SEQUENCE: 2

Ile Ser Thr Asp Gly Met Ser Thr
1               5


<210> SEQ ID NO 3
<211> LENGTH: 15
<212> TYPE: PRT
<213> ORGANISM: Artificial
<220> FEATURE:
<223> OTHER INFORMATION: CR8097 VH CDR3

<400> SEQUENCE: 3

Val Arg Gly Ser Thr Tyr Tyr Phe Gly Ser Gly Ser Leu Asn Phe
1               5                   10                  15


<210> SEQ ID NO 4
<211> LENGTH: 9
<212> TYPE: PRT
<213> ORGANISM: Artificial
<220> FEATURE:
<223> OTHER INFORMATION: CR8097 VL CDR1
```

<400> SEQUENCE: 4

Asn Ser Asp Ile Gly Asn Tyr Asp Tyr
1 5

<210> SEQ ID NO 5
<211> LENGTH: 3
<212> TYPE: PRT
<213> ORGANISM: Artificial Sequence
<220> FEATURE:
<223> OTHER INFORMATION: CR8097 VL CDR2

<400> SEQUENCE: 5

Asp Val Ser
1

<210> SEQ ID NO 6
<211> LENGTH: 11
<212> TYPE: PRT
<213> ORGANISM: Artificial
<220> FEATURE:
<223> OTHER INFORMATION: CR8097 VL CDR3

<400> SEQUENCE: 6

Ser Ser Tyr Ala Gly Thr Phe Thr Tyr Val Val
1 5 10

<210> SEQ ID NO 7
<211> LENGTH: 122
<212> TYPE: PRT
<213> ORGANISM: Artificial
<220> FEATURE:
<223> OTHER INFORMATION: CR8097 VH

<400> SEQUENCE: 7

Glu Val Gln Leu Val Glu Ser Gly Gly Gly Leu Val Gln Pro Gly Gly
1 5 10 15

Ser Leu Arg Val Ser Cys Glu Val Ser Gly Phe Thr Phe Ser Asn Asn
20 25 30

Trp Met His Trp Val Arg Gln Ala Pro Gly Lys Gly Pro Val Trp Val
35 40 45

Ser Arg Ile Ser Thr Asp Gly Met Ser Thr Ser Tyr Ala Glu Phe Val
50 55 60

Lys Gly Arg Phe Thr Ile Ser Arg Asp Asn Ala Arg Asn Thr Leu Tyr
65 70 75 80

Leu Gln Met Asn Ser Leu Arg Asp Glu Asp Thr Ala Val Tyr Tyr Cys
85 90 95

Val Arg Gly Ser Thr Tyr Tyr Phe Gly Ser Gly Ser Leu Asn Phe Trp
100 105 110

Gly Gln Gly Thr Thr Val Ile Val Ser Ser
115 120

<210> SEQ ID NO 8
<211> LENGTH: 111
<212> TYPE: PRT
<213> ORGANISM: Artificial
<220> FEATURE:
<223> OTHER INFORMATION: CR8097 VL

<400> SEQUENCE: 8

Gln Ser Ala Leu Thr Gln Pro Arg Ser Val Ser Gly Ser Pro Gly Gln
1 5 10 15

Ser Val Thr Ile Ser Cys Thr Gly Thr Asn Ser Asp Ile Gly Asn Tyr

-continued

```
            20                  25                  30

Asp Tyr Val Ser Trp Tyr Gln Gln His Pro Gly Lys Ala Pro Arg Leu
        35                  40                  45

Ile Ile Tyr Asp Val Ser Glu Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Phe Cys Ser Ser Tyr Ala Gly Thr
                85                  90                  95

Phe Thr Tyr Val Val Phe Gly Gly Gly Thr Lys Leu Thr Val Leu
            100                 105                 110


<210> SEQ ID NO 9
<211> LENGTH: 452
<212> TYPE: PRT
<213> ORGANISM: Artificial
<220> FEATURE:
<223> OTHER INFORMATION: CR8097 HC

<400> SEQUENCE: 9

Glu Val Gln Leu Val Glu Ser Gly Gly Gly Leu Val Gln Pro Gly Gly
1               5                   10                  15

Ser Leu Arg Val Ser Cys Glu Val Ser Gly Phe Thr Phe Ser Asn Asn
            20                  25                  30

Trp Met His Trp Val Arg Gln Ala Pro Gly Lys Gly Pro Val Trp Val
        35                  40                  45

Ser Arg Ile Ser Thr Asp Gly Met Ser Thr Ser Tyr Ala Glu Phe Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Arg Asp Glu Asp Thr Ala Val Tyr Tyr Cys
                85                  90                  95

Val Arg Gly Ser Thr Tyr Tyr Phe Gly Ser Gly Ser Leu Asn Phe Trp
            100                 105                 110

Gly Gln Gly Thr Thr Val Ile Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

-continued

```
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 10
<211> LENGTH: 217
<212> TYPE: PRT
<213> ORGANISM: Artificial
<220> FEATURE:
<223> OTHER INFORMATION: CR8097 LC

<400> SEQUENCE: 10

Gln Ser Ala Leu Thr Gln Pro Arg Ser Val Ser Gly Ser Pro Gly Gln
1               5                   10                  15

Ser Val Thr Ile Ser Cys Thr Gly Thr Asn Ser Asp Ile Gly Asn Tyr
            20                  25                  30

Asp Tyr Val Ser Trp Tyr Gln Gln His Pro Gly Lys Ala Pro Arg Leu
        35                  40                  45

Ile Ile Tyr Asp Val Ser Glu Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Phe Cys Ser Ser Tyr Ala Gly Thr
                85                  90                  95

Phe Thr Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
```

-continued

```
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 11
<211> LENGTH: 226
<212> TYPE: PRT
<213> ORGANISM: Artificial
<220> FEATURE:
<223> OTHER INFORMATION: HBsAg ayw_wt

<400> SEQUENCE: 11

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225


<210> SEQ ID NO 12
<211> LENGTH: 226
<212> TYPE: PRT
<213> ORGANISM: Artificial
<220> FEATURE:
<223> OTHER INFORMATION: HBsAg adr_wt

<400> SEQUENCE: 12

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30
```

-continued

```
Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 13
<211> LENGTH: 226
<212> TYPE: PRT
<213> ORGANISM: Artificial
<220> FEATURE:
<223> OTHER INFORMATION: Consensus seq. Fig.3
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (125)..(127)
<223> OTHER INFORMATION: Xaa can be any naturally occurring amino acid
<220> FEATURE:

-continued

```
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (159)..(160)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid

<400> SEQUENCE: 13

Met Glu Xaa Xaa Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Xaa Xaa Xaa Cys
        35                  40                  45

Xaa Gly Gln Asn Ser Gln Ser Pro Thr Ser Asn His Ser Pro Thr Ser
    50                  55                  60

Cys Pro Pro Xaa Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Xaa Pro Gly
            100                 105                 110

Xaa Ser Thr Thr Ser Thr Gly Pro Cys Xaa Thr Cys Xaa Xaa Xaa Ala
        115                 120                 125

Gln Gly Thr Ser Met Xaa Pro Ser Cys Cys Cys Thr Lys Pro Ser Asp
    130                 135                 140

Gly Asn Cys Thr Cys Ile Pro Ile Pro Ser Ser Trp Ala Phe Xaa Xaa
145                 150                 155                 160

Phe Leu Trp Glu Trp Ala Ser Xaa Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Xaa Ile
        195                 200                 205

Leu Ser Pro Phe Leu Pro Leu Leu Pro Ile Phe Phe Cys Leu Trp Val
    210                 215                 220

Tyr Ile
225
```

HUMAN BINDING MOLECULES CAPABLE OF BINDING TO AND NEUTRALIZING HEPATITIS B VIRUSES AND USES THEREOF

CROSS-REFERENCE TO RELATED APPLICATIONS

This application is a national phase entry under 35 U.S.C. §371 of International Patent Application PCT/EP2013/069828, filed Sep. 24, 2013, designating the United States of America and published in English as International Patent Publication WO 2014/048910 A1 on Apr. 3, 2014, which claims the benefit under Article 8 of the Patent Cooperation Treaty and under 35 U.S.C. §119 to European Application Serial No. 12186261.9, filed Sep. 27, 2012, and U.S. Provisional Patent Application Ser. No. 61/706,518, filed Sep. 27, 2012.

TECHNICAL FIELD

The disclosure relates to medicine and biotechnology. The disclosure, in particular, relates to human binding molecules, e.g., monoclonal antibodies or antigen-binding fragments thereof, capable of binding to and neutralizing Hepatitis B viruses. In addition, the disclosure relates to the diagnosis, prophylaxis and/or treatment of infections caused by Hepatitis B virus.

BACKGROUND

Hepatitis B Virus (HBV) has infected more than 2 billion people around the world and causes temporary and chronic liver diseases. Although a vaccine against HBV was introduced in 1982, globally 350 million people are infected chronically. The risk of chronic infection is correlated with patient's age at time of infection. Infection persists in about 90% of infants infected during the first year of life. In contrast, infection persists only in 1-5% of patients infected as adults.

Active replication of HBV is characterized by liver damage, most likely due to immune reactivity. Chronic HBV infection can lead to liver cancer and dead. About 25% of adults who become chronically infected during childhood die from HBV-related liver cirrhosis or cancer, an estimated 500,000 to 1.2 million persons each year.

The immune response to HBV consists of both a cellular immune response for the elimination of HBV infected cells, as well as a humoral antibody response, which contributes to the clearance of circulating virus particles. The major viral component responsible for the induction of neutralizing HBV antibodies is the small HBV surface antigen (HBsAg).

All recombinant vaccines contain HBsAg and the efficacy of these vaccines is high (protection in more than 95% of infants, children and young adults) and long lasting (>20 years). In addition, all vaccines elicit the immunity across serotypes. HBsAg consists of 226 amino acids, with one N-linked glycosylation site. Comparison of circulating HBV strains has shown that there is a high level of homogeneity between the various HBsAg sequences.

There are various anti-viral products on the market for the treatment of a chronic HBV infection. However, none of the available anti-viral drugs can clear infection; they only inhibit replication, thus, minimizing liver damage. Therefore, liver transplantation is the only treatment option for patients with HBV end-stage liver disease. HBV-diseased livers are estimated to represent 5% of all liver transplants in the United States while in China, around 85% of all liver transplantations are due to HBV infection.

To prevent re-infection of the new liver after liver transplantation, patients are currently treated with polyclonal HBV immunoglobulin (HBIg) combined with an antiviral agent. Polyclonal HBIg is prepared from pooled plasma from immunized donors and is also used as post exposure prophylaxis either as stand alone or in combination with a vaccine. HBIg preparations are indicated for the treatment of acute exposure to blood containing HBsAg, perinatal exposure of infants born to HBsAg-positive mothers, sexual exposure to HBsAg positive persons, and household exposure to persons with acute hepatitis B virus infection. Since there are some limitations associated with HBIg like availability, cost of goods, large injection volumes, adverse events, and the risk of blood-borne infection, there is a medical need for a monoclonal antibody product against HBV.

Several monoclonal antibodies against HBV have been described previously. PCT patent application PCT/IL97/00183 and PCT/IL97/00184, respectively, disclose human monoclonal antibody mAb 17.1.41 and mAb 19.79.5, against HBV surface antigen. These antibodies bind to various HBV subtypes. However, HBsAg of subtype adw2 (genotype C) is not recognized by the antibodies (Eren et al., 2000, Hepatology 32, 588). Genotype C is highly prevalent in China where the majority of chronically infected individuals reside.

PCT Patent Application WO2009069917 discloses a human antibody capable of neutralizing hepatitis B virus for the prevention and treatment of hepatitis B infection. It has not been demonstrated that this antibody binds to all major sero- and genotypes of HBV. In addition, none of the antibodies disclosed hitherto have been shown to neutralize the majority of commonly known vaccine-induced and anti-viral-induced escape mutants.

Thus, there is a need in the art for antibodies that bind and neutralize a large breadth of sero- and genotypes of HBV in addition to possible escape mutants and which can be manufactured on large industrial scale.

BRIEF SUMMARY

Provided are binding molecules, in particular human binding molecules, capable of specifically binding to and neutralizing Hepatitis B virus (HBV). Provided are binding molecules that bind to the major sero- and genotypes of HBV, thereby, offering broad protection. In addition, the binding molecules hereof bind to all major vaccine-induced and anti-viral-induced HBV escape mutants. Finally, the binding molecules against HBV of the disclosure can be manufactured efficiently on large scale, which make them appropriate for industrial production.

The binding molecules, according to the disclosure, comprise a heavy chain CDR1 comprising the amino acid sequence of SEQ ID NO:1, a heavy chain CDR2 comprising the amino acid sequence of SEQ ID NO:2, a heavy chain CDR3 comprising the amino acid sequence of SEQ ID NO:3, a light chain CDR1 comprising the amino acid sequence of SEQ ID NO:4, a light chain CDR2 comprising the amino acid sequence of SEQ ID NO:5, and a light chain CDR3 comprising the amino acid sequence of SEQ ID NO:6.

In a certain embodiment, the binding molecules of the disclosure comprise a heavy chain variable region comprising the amino acid sequence (or peptide) of SEQ ID NO:7 and a light chain variable region comprising the amino acid sequence of SEQ ID NO:8.

In another embodiment, the binding molecules of the disclosure comprise a heavy chain comprising the amino acid sequence of SEQ ID NO:9 and a light chain comprising the amino acid sequence of SEQ ID NO:10.

The disclosure also pertains to binding molecules that specifically compete for binding to an epitope on a Hepatitis B virus protein with a binding molecule according to the disclosure.

Preferably, the binding molecules, according to the disclosure, are human monoclonal antibodies, or antigen-binding fragments thereof.

The disclosure also pertains to immunoconjugates, comprising at least one binding molecule, according to the disclosure, and further comprising at least one tag.

Another aspect of the disclosure relates to nucleic acid molecules encoding a binding molecule according to the disclosure.

The binding molecules, immunoconjugates and/or nucleic acid molecules of the disclosure are suitable for use as a medicament, preferably, for use in the diagnosis, prophylaxis and/or treatment of a Hepatitis B infection caused by a Hepatitis B virus subtype.

The disclosure also pertains to a functional variant of a binding molecule according to the disclosure.

The disclosure also pertains to pharmaceutical compositions comprising a binding molecule, according to the disclosure, and/or an immunoconjugate, and a pharmaceutically acceptable carrier or excipient.

The disclosure also pertains to pharmaceutical composition comprising a binding molecule, according to the disclosure, and an additional Hepatitis B neutralizing binding molecule.

Another aspect of the disclosure relates to a method of detecting a Hepatitis B virus infection comprising:

(a) Assaying the level of Hepatitis B virus antigen in a biological sample using a binding molecule, and/or an immunoconjugate, according to the disclosure; and (b) Comparing the assayed level of Hepatitis B virus antigen with a control level wherein an increase in the assayed level of Hepatitis B virus antigen compared to the control level of the Hepatitis B virus antigen is indicative of a Hepatitis B virus infection.

DETAILED DESCRIPTION

Figure 1:
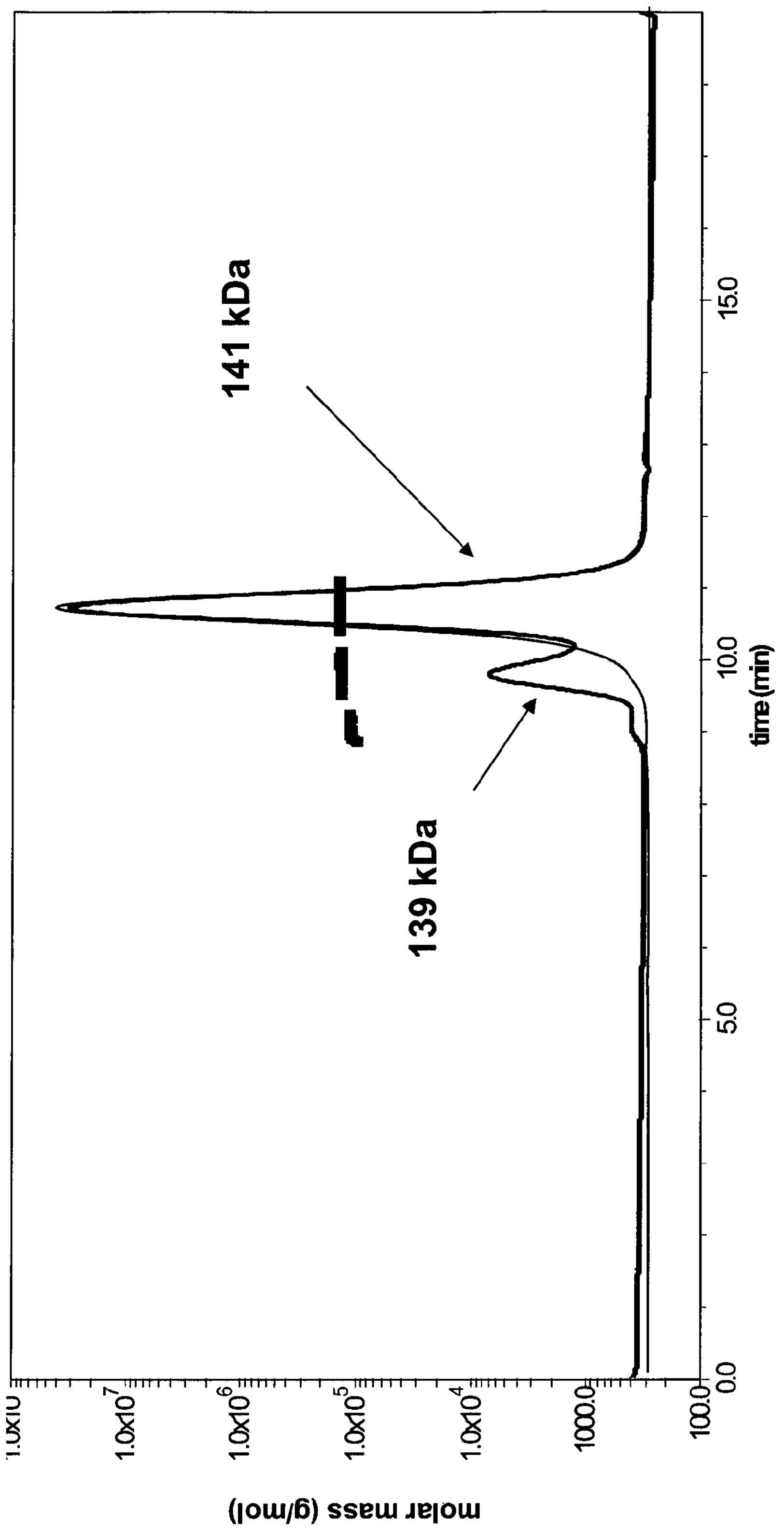
FIG. 1 Overlay of the HP-SEC profiles of CR8096 (thick line with separate peaks) and CR8097 (thin line with single peak) and assignment of the molecular mass as determined by MALS detection.

Definitions of terms as used in the disclosure are given below.

The term “included” or “including,” as used herein, is deemed to be followed by the words “without limitation.”

As used herein, the term “binding molecule” refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin. Regardless of structure, the antigen-binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the binding molecule.

The term “binding molecule,” as used herein, includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses, e.g., IgA1, IgA2, IgG1, IgG2, IgG3 and IgG4.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. A binding molecule or antigen-binding fragment, thereof, may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is, therefore, applied in definition to the naked or unconjugated binding molecule in vitro, not in vivo.

As used herein, the term "biological sample" encompasses a variety of sample types, including blood and other liquid samples of biological origin, solid tissue samples such as a biopsy specimen or tissue cultures, or cells derived there from and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

The term "complementarity determining regions" (CDR), as used herein, means sequences within the variable regions of binding molecules, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

The term "deletion," as used herein, denotes a change in either amino acid or nucleotide sequence in which one or more amino acid or nucleotide residues, respectively, are absent as compared to the reference, often the naturally occurring, molecule.

The term "expression-regulating nucleic acid sequence," as used herein, refers to polynucleotide sequences necessary for and/or affecting the expression of an operably linked coding sequence in a particular host organism. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

The term "functional variant," as used herein, refers to a nucleic acid molecule or binding molecule that comprises a nucleotide and/or amino acid sequence that is altered by one or more nucleotides and/or amino acids compared to the nucleotide and/or amino acid sequences of the reference nucleic acid molecule or binding molecule. A functional variant of a binding molecule, according to the disclosure, is capable of competing for binding to the binding partner, i.e., the Hepatitis B virus, with the reference binding molecule. In other words, the modifications in the amino acid and/or nucleotide sequence of the reference binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), non-polar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that also other classifications of amino acid residue families than the one used above can be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

The term Hepatitis B virus "serotype" specifically includes all individual Hepatitis B virus strains within a certain serotype. Serotypic classification of an HBV virus strain is based on a limited number of amino acid residues in the HBsAg molecule via an algorithm/decision tree (Purdy et al., 2007 Intervirology). To date eleven serotypes of HBV have been described, being adw1, adw2, adw3, adw4q+, adw4q−, adrq+, adrq−, ayw1, ayw2, ayw3, ayw4. Serotypes may also be referred to as "subtypes." Accordingly, as used herein, the terms "serotypes" and "subtypes" may be used interchangeably.

The term HBV "genotypes" specifically includes all individual HBV virus strains within each genotype. Classification of HBV genotypes is based on the phylogenetic relatedness of the entire HBV genome. HBV genomes within a certain genotype show by definition less than 4% sequence divergence within a phylogenetic clade and more than 8% divergence with extra-clade sequences. To date nine HBV genotypes, designated A to I, have been defined.

The term "neutralizing," as used herein, in relation to the binding molecule of the disclosure refers to a binding molecule that inhibits a Hepatitis B virus from replication, in vitro and/or within a subject, regardless of the mechanism by which neutralization is achieved. Thus, neutralization can, e.g., be achieved by inhibiting the attachment or adhesion of the virus to the cell surface, or by inhibition of the fusion of viral and cellular membranes following attachment of the virus to the target cell, or by inhibiting viral egress from infected cells, and the like.

The term "cross-neutralizing" or "cross-neutralization," as used herein, in relation to the binding molecules of the disclosure refers to the ability of the binding molecules of the disclosure to neutralize different serotypes and/or genotypes of Hepatitis B viruses.

The term "host," as used herein, is intended to refer to an organism or a cell into which a vector such as a cloning vector or an expression vector has been introduced. The organism or cell can be prokaryotic or eukaryotic. Preferably, the hosts isolated host cells, e.g., host cells in culture. The term "host cells" merely signifies that the cells are modified for the (over)-expression of the binding molecule of the disclosure and include B-cells that originally express these binding molecule and which cells have been modified to over-express the binding molecule by immortalization, amplification, enhancement of expression, etc. It should be understood that the term host is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host," as used herein.

The term "human," when applied to binding molecules as defined herein, refers to molecules that are either directly derived from a human or based upon a human germ line sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo).

"Based on," as used herein, refers to the situation that a nucleic acid sequence may be exactly copied from a template, or with minor mutations, such as by error-prone PCR methods, or synthetically made matching the template exactly or with minor modifications.

The term "insertion," also known as the term "addition," denotes a change in an amino acid or nucleotide sequence resulting in the addition of one or more amino acid or nucleotide residues, respectively, as compared to the parent sequence.

The term "isolated," when applied to binding molecules, as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium components, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules, as defined herein, is intended to refer to nucleic acid molecules in which the nucleotide sequences encoding the binding molecules are free of other nucleotide sequences, particularly nucleotide sequences encoding binding molecules that bind other binding partners. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material or culture medium when produced by recombinant techniques, or substantially free of chemical precursors or other chemicals when chemically synthesized.

The term "monoclonal antibody," as used herein, refers to a preparation of antibody molecules of single specificity. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant for the binding specificity.

The term "naturally occurring," as used herein, as applied to an object refers to the fact that an object or compound can be found in nature. For example, a polypeptide or polynucleotide sequence that is present in an organism that can be isolated from a source in nature and which has not been intentionally modified by man in the laboratory is naturally occurring.

The term "nucleic acid molecule," as used in the disclosure, refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the used dosages and concentrations, and is compatible with other ingredients of the formulation comprising the drug, agent or binding molecule. Pharmaceutically acceptable excipients are widely applied and known in the art.

The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigenic determinant or epitope and not immunospecifically binding to other antigenic determinants or epitopes. A binding molecule that specifically binds to an antigen may bind to other peptides or polypeptides with lower affinity as determined by endpoint assays such as radioimmunoassays (RIA) or enzyme-linked immunosorbent assays (ELISA) or label-free technologies such as SPR, BLI or other assays known in the art. Binding molecules or fragments, thereof, that immunospecifically bind to an antigen may be cross-reactive with related antigens, carrying the same epitope. Preferably, binding molecules or fragments, thereof, that immunospecifically bind to an antigen do not cross-react with other antigens.

A "substitution," as used herein, denotes the replacement of one or more amino acids or nucleotides by different amino acids or nucleotides, respectively.

The term "therapeutically effective amount" refers to an amount of the binding molecule, as defined herein, which is effective for preventing, ameliorating and/or treating a condition resulting from infection with a Hepatitis B virus. Ameloriation, as used herein, may refer to the reduction of visible or perceptible disease symptoms, viremia, or any other measurable manifestation of Hepatitis B infection.

The term "treatment" refers to therapeutic treatment as well as prophylactic or preventative measures to cure or halt or at least retard disease progress. Those in need of treatment include those already inflicted with a condition resulting from infection with Hepatitis B virus as well as those in which infection with Hepatitis B virus is to be prevented. Subjects partially or totally recovered from infection with Hepatitis B virus might also be in need of treatment. Prevention encompasses inhibiting or reducing the spread of Hepatitis B virus or inhibiting or reducing the onset, development or progression of one or more of the symptoms associated with infection with Hepatitis B virus.

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

In a first aspect, the disclosure provides binding molecules capable of specifically binding to Hepatitis B virus strains, and capable of neutralizing the Hepatitis B virus strains. The binding molecules are capable of neutralizing Hepatitis B viruses both in vitro and in vivo.

The binding molecules, according to the disclosure, comprise a heavy chain which comprises the CDR sequences set forth in SEQ ID NO:1-3 and a light chain which comprises the CDR sequences set forth in SEQ ID NO:4-6. According to the disclosure, CDR regions are determined according to Kabat et al., (1991) as described in Sequences of Proteins of Immunological Interest.

Thus, the disclosure provides binding molecules capable of specifically binding to a Hepatitis B virus and capable of neutralizing Hepatitis B virus, wherein the binding molecules comprises a heavy chain CDR1 comprising the amino acid sequence of SEQ ID NO:1, a heavy chain CDR2 comprising the amino acid sequence of SEQ ID NO:2, and a heavy chain CDR3 comprising the amino acid sequence of SEQ ID NO:3, and a light chain CDR1 comprising the amino acid sequence of SEQ ID NO:4, a light chain CDR2 comprising the amino acid sequence of SEQ ID NO:5, and a light chain CDR3 comprising the amino acid sequence of SEQ ID NO:6.

In a certain embodiment, the binding molecules of the disclosure comprise a heavy chain variable region comprising the amino acid sequence of SEQ ID NO:7, and a light chain variable region comprising the amino acid sequence of SEQ ID NO:8. In another embodiment, the binding molecules of the disclosure comprise a heavy chain comprising the amino acid sequence of SEQ ID NO:9 and a light chain comprising the amino acid sequence of SEQ ID NO:10.

Preferably, the binding molecules, according to the disclosure, are human binding molecules. In a preferred embodiment, the binding molecules are human monoclonal antibodies, or antigen-binding fragments thereof.

The binding molecules of the disclosure may be capable of specifically binding to Hepatitis B viruses that are viable, living and/or infective or that are in inactivated/attenuated form. Methods for inactivating/attenuating virus, e.g., Hepatitis B viruses are well known in the art and include, but are not limited to, treatment with formalin, β-propiolactone (BPL), merthiolate, and/or ultraviolet light.

The binding molecules of the disclosure may also be capable of specifically binding to one or more fragments of the Hepatitis B viruses, such as inter alia, a preparation of one or more proteins and/or (poly)peptides, derived from subtypes of Hepatitis B viruses or one or more recombinantly produced proteins and/or polypeptides of Hepatitis B viruses. The nucleotide and/or amino acid sequence of proteins of various Hepatitis B strains can be found in the GenBank-database. The HBsAg sequences used in this study were selected from the large Japanese NIG HBV database, which contains more than 6000 HBV sequences (for link see the World Wide Web at s2as02.genes.nig.ac.jp/. It is well within the reach of the skilled person to find such sequences in the respective databases.

The binding molecules of the disclosure are capable of binding to HBsAg peptides from at least the following serotypes: adw2 (genotype B), ayw2 (genotype D), ayw1 (genotype B), adrq− (genotype C), ayr (genotype C), adw4q+ (genotype A), adrq+ (genotype C), ayw4 (genotype D), adw4q− (genotype F), adw3, ayw3 (genotype D), adw2 (genotype I), ayw1 (genotype A), adw2 (genotype A), adw2 (genotype C). This was illustrated in example 2. Herewith, the binding molecules of the disclosure surprisingly offer a very broad protection by binding to the major sero- and genotypes of HBV.

In another embodiment, the binding molecules of the disclosure are capable of specifically binding to a fragment of the above-mentioned proteins and/or polypeptides, wherein the fragment at least comprises an epitope recognized by the binding molecules of the disclosure. An "epitope," as used herein, is a moiety that is capable of binding to a binding molecule of the disclosure with sufficiently high affinity to form a detectable antigen-binding molecule complex.

In addition, the binding molecules, according to the disclosure, surprisingly bind to all major vaccine-induced and anti-viral-induced HBV escape mutants in HBsAg such as, e.g., P120T, Q129R, M133I, D144R, G145R, G145A, E164D, I195M, W196S (example 3). Therefore, the binding molecules of the disclosure can be used universally against HBV.

The binding molecules of the disclosure can be intact immunoglobulin molecules such as monoclonal antibodies, or the binding molecules can be antigen-binding fragments thereof, including, but not limited to, heavy and light chain variable regions, Fab, F(ab'), $F(ab)_2$, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to Hepatitis B virus strains or a fragment thereof. In a preferred embodiment, the binding molecules of the disclosure are human monoclonal antibodies, and/or antigen-binding fragments thereof. The binding molecules may also be nanobodies, alphabodies, affibodies, FN3-domain scaffolds and other scaffolds based on domains in (human) repeat proteins, like Adnectins, Anticalins, Darpins, Centyrins, etc., or other scaffolds comprising epitope binding sequences.

The binding molecules of the disclosure can be used in non-isolated or isolated form. Furthermore, the binding molecules of the disclosure can be used alone or in a mixture comprising at least one binding molecule (or variant or fragment thereof) of the disclosure, and one or more other binding molecules that bind to Hepatitis B and have Hepatitis B virus inhibiting effect. In other words, the binding molecules can be used in combination, e.g., as a pharmaceutical composition comprising two or more binding molecules, variants or fragments thereof. For example, binding molecules having different, but complementary activities, can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. Optionally, the mixture may also comprise at least one binding molecule, according to the disclosure, and at least one other therapeutic agent. Preferably, the therapeutic agent such as, e.g., nucleoside analogues (e.g., lamivudine, adefovir) and/or immunomodulatory agents (e.g., interferon-based therapy) are useful in the prophylaxis and/or treatment of a hepatitis B virus infection.

Typically, binding molecule, according to the disclosure, can bind to its binding partners, i.e., an Hepatitis B virus, and/or fragments thereof, with an equilibrium dissociation constant ($K_D$) that is lower than $0.2\times10^{-4}$ M, $1.0\times10^{-5}$ M, $1.0\times10^{-6}$ M, $1.0\times10^{-7}$ M, preferably lower than $1.0\times10^{-8}$ M, more preferably lower than $1.0\times10^{-9}$ M, more preferably lower than $1.0\times10^{-10}$ M, even more preferably lower than $1.0\times10^{-11}$ M, and in particular lower than $1.0\times10^{-12}$ M. The equilibrium dissociation constant can vary for antibody isotypes. For example, binding for an IgM isotype refers to an equilibrium dissociation constant of at least about $1.0\times10^{-7}$ M. Binding kinetics can, for instance, be obtained using label-free technologies such as surface plasmon resonance or biolayer interferometry.

The binding molecules of the disclosure exhibit neutralizing activity. Neutralizing activity can, for instance, be measured as described herein. Typically, the binding molecules, according to the disclosure, have a neutralizing activity of 1000 ng/ml or less, preferably 500 ng/ml or less, more preferably a neutralizing activity of 100 ng/ml or less, even more preferably 10 ng/ml or less, as determined in an in vitro virus neutralization assay (VNA) as described in examples 4 and 5. The binding molecules, according to the disclosure, may bind to Hepatitis B virus or a fragment thereof in soluble form such as, for instance, in a sample or in suspension or may bind to Hepatitis B viruses or fragments thereof, bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to Hepatitis B viruses in purified/isolated or non-purified/non-isolated form.

As discussed above, the disclosure in certain embodiments provides isolated human binding molecules that are able to recognize and bind to an epitope on the Hepatitis B viruses, wherein the binding molecules have neutralizing activity against Hepatitis B viruses, both in vitro and in vivo.

Another aspect of the disclosure includes functional variants of the binding molecule as defined above. Molecules are considered to be functional variants of a binding molecule, according to the disclosure, if the variant binding molecules are capable of competing for immunospecifically binding to a Hepatitis B virus or a fragment thereof with the "parental" or "reference" binding molecules. In other words, molecules are considered to be functional variants of a binding molecule, according to the disclosure, when the functional variants are still capable of binding to the same or overlapping epitope of the Hepatitis B virus or a fragment thereof. For the sake of this application "parental" and "reference" will be used as synonyms meaning that the information of the reference or parental molecule, or the physical molecule itself may form the basis for the variation. Functional variants include, but are not limited to, derivatives that are substantially similar in primary structural sequence, including those that have modifications in the Fc receptor or other regions involved with effector functions, and/or which contain, e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like. Alternatively, functional variants can be binding molecules, as defined in the disclosure, comprising an amino acid sequence containing substitutions, insertions, deletions or combinations thereof, of one or more amino acids compared to the amino acid sequences of the parental binding molecules. Furthermore, functional variants can comprise truncations of the amino acid sequence at either or both the amino or carboxyl termini. Functional variants, according to the disclosure, may have the same or different, either higher or lower, binding potencies compared to the parental binding molecule but are still capable of binding to the Hepatitis B virus or a fragment thereof. For instance, functional variants, according to the disclosure, may have increased or decreased binding potencies for a Hepatitis B virus or a fragment thereof, compared to the parental binding molecules. In certain embodiments, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the disclosure have at least about 80% to about 99%, preferably at least about 70% to about 99%, more preferably at least about 80% to about 99%, even more preferably at least about 90% to about 99%, most preferably at least about 95% to about 99%, in particular at least about 97% to about 99% amino acid sequence identity and/or homology with the parental binding molecules as defined herein. Computer algorithms such as inter alia Gap or Bestfit, known to a person skilled in the art, can be used to optimally align amino acid sequences to be compared and to define similar or identical amino acid residues. Functional variants can be obtained by altering the parental binding molecules or parts thereof by general molecular biology methods known in the art including, but not limited to, error-prone PCR, oligonucleotide-directed mutagenesis, site-directed mutagenesis and heavy and/or light chain shuffling.

In certain embodiment, the functional variants of the disclosure have neutralizing activity against Hepatitis B viruses. The neutralizing activity may either be identical, or be higher or lower compared to the parental binding molecules. As used in this application, when the term (human) binding molecule is used, this also encompasses functional variants of the (human) binding molecule. In certain embodiments, the functional variants are binding molecules comprising a heavy chain variable sequence comprising one or more amino acid mutations, such as one, two, three, four, five, six, seven, eight, nine, ten, eleven, twelve, thirteen, fourteen or fifteen amino acid mutations, as compared to SEQ ID NO:7 and/or a light chain variable region comprising one or more amino acid mutations, such as one, two, three, four, five, six, seven, eight, nine, ten, eleven, twelve, thirteen, fourteen or fifteen amino acid mutations as compared to SEQ ID NO:8.

In certain embodiments, the binding molecules, according to the disclosure, are for a use as a medicament, and preferably for use in the therapeutic and/or prophylactic treatment of a Hepatitis B infection caused by Hepatitis B viruses from different sero- and genotypes.

The disclosure also relates to pharmaceutical compositions comprising at least one binding molecule, according to the disclosure, and at least a pharmaceutically acceptable excipient.

In yet another embodiment, the disclosure relates to the use of a binding molecule, according to the disclosure, in the preparation of a medicament for the prophylaxis, and/or treatment of a Hepatitis B virus infection. In particular, the binding molecules, according to the disclosure, are used for preventing re-infection with Hepatitis B virus of a freshly transplanted liver.

In yet a further aspect, the disclosure provides immunoconjugates, i.e., molecules comprising at least one binding molecule, as defined herein, and further comprising at least one tag, such as inter alia a detectable moiety/agent. Also contemplated in the disclosure are mixtures of immunoconjugates, according to the disclosure, or mixtures of at least one immunoconjugates, according to the disclosure, and another molecule, such as a therapeutic agent or another binding molecule or immunoconjugate. In further embodiments, the immunoconjugates of the disclosure may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates of the disclosure may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject has been infected with an Hepatitis B virus or to monitor the development or progression of an Hepatitis B virus infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the human binding molecules or immunoconjugates of the disclosure can also be attached to solid supports, which are particularly useful for in vitro immunoassays or purification of Hepatitis B viruses or fragments thereof. Such solid supports might be porous or nonporous, planar or non-planar. The binding molecules of the disclosure can be fused to marker sequences, such as a peptide to facilitate purification. Alternatively, an antibody can be conjugated to a second antibody to form an antibody heteroconjugate. In another aspect the binding molecules of the disclosure may be conjugated/attached to one or more antigens. Preferably, these antigens are antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules of the disclosure will bind to Hepatitis B virus and the antigens attached to the binding molecules will initiate a powerful T-cell attack on the conjugate, which will eventually lead to the destruction of the Hepatitis B virus.

Next to producing immunoconjugates chemically by conjugating, directly or indirectly, via, for instance, a linker, the immunoconjugates can be produced as fusion proteins comprising the binding molecules of the disclosure and a suitable tag. Fusion proteins can be produced by methods known in the art such as, e.g., recombinantly by constructing nucleic acid molecules comprising nucleotide sequences encoding the binding molecules in frame with nucleotide sequences encoding the suitable tag(s) and then expressing the nucleic acid molecules.

It is another aspect of the disclosure to provide nucleic acid molecules encoding at least a binding molecule, functional variant or immunoconjugate, according to the disclosure. Such nucleic acid molecules can be used as intermediates for cloning purposes, e.g., in the process of affinity maturation as described above. In a preferred embodiment, the nucleic acid molecules are isolated or purified.

The skilled man will appreciate that functional variants of these nucleic acid molecules are also intended to be a part of the disclosure. Functional variants are nucleic acid sequences that can be directly translated, using the standard genetic code, to provide an amino acid sequence identical to that translated from the parental nucleic acid molecules.

Preferably, the nucleic acid molecules encode binding molecules comprising the CDR regions as described above. In a further embodiment, the nucleic acid molecules encode binding molecules comprising two, three, four, five or even all six CDR regions of the binding molecules of the disclosure.

In another embodiment, the nucleic acid molecules encode binding molecules comprising a heavy chain comprising the variable heavy chain sequences as described above. In another embodiment, the nucleic acid molecules encode binding molecules comprising a light chain comprising the variable light chain sequences as described above. The nucleotide sequences and the amino acid sequences of the heavy and light chain variable regions of the binding molecules of the disclosure are given below.

It is another aspect of the disclosure to provide vectors, i.e., nucleic acid constructs, comprising one or more nucleic acid molecules, according to the disclosure. Vectors can be derived from plasmids such as inter alia F, R1, RP1, Col, pBR322, TOL, Ti, etc.; cosmids; phages such as lambda, lambdoid, M13, Mu, P1, P22, Qβ, T-even, T-odd, T2, T4, T7, etc.; plant viruses. Vectors can be used for cloning and/or for expression of the binding molecules of the disclosure and might even be used for gene therapy purposes. Vectors comprising one or more nucleic acid molecules, according to the disclosure, operably linked to one or more expression-regulating nucleic acid molecules are also covered by the disclosure. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the disclosure as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules, as described above, operably linked to one or more nucleic acid molecules encoding proteins or peptides that can be used to isolate the human binding molecules are also covered by the disclosure. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional aspect of the disclosure. Preferably, the hosts are host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the disclosure. Mammalian cells provide expressed proteins with posttranslational modifications that are most similar to natural molecules of mammalian origin. Since the disclosure deals with molecules that may have to be administered to humans, a completely human expression system would be particularly preferred. Therefore, even more preferably, the host cells are human cells.

Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

A method of producing a binding molecule, according to the disclosure, is an additional aspect of the disclosure. The method comprises the steps of a) culturing a host, according to the disclosure, under conditions conducive to the expression of the binding molecule, and b) optionally, recovering the expressed binding molecule. The expressed binding molecules can be recovered from the cell free extract, but preferably they are recovered from the culture medium. The above method of producing can also be used to make functional variants of the binding molecules and/or immunoconjugates of the disclosure. Methods to recover proteins, such as binding molecules, from cell free extracts or culture medium are well known to the man skilled in the art. Binding molecules, functional variants and/or immunoconjugates obtainable by the above-described method are also a part of the disclosure.

Alternatively, next to the expression in hosts, such as host cells, the binding molecules and immunoconjugates of the disclosure can be produced synthetically by conventional peptide synthesizers or in cell-free translation systems using RNA nucleic acid derived from DNA molecules, according to the disclosure. Binding molecules and immunoconjugates as obtainable by the above-described synthetic production methods or cell-free translation systems are also a part of the disclosure.

In yet another embodiment, binding molecules of the disclosure can also be produced in transgenic, non-human, mammals such as inter alia rabbits, goats or cows, and secreted into, for instance, the milk thereof.

In yet another alternative embodiment, binding molecules, according to the disclosure, may be generated by transgenic non-human mammals, such as, for instance, transgenic mice or rabbits that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of Hepatitis B virus, HBsAg or a fragment thereof. Protocols for immunizing non-human mammals are well established in the art. See Using Antibodies: A Laboratory Manual, Edited by: E. Harlow, D. Lane (1998), Cold Spring Harbor Laboratory, Cold Spring Harbor, N.Y. and Current Protocols in Immunology, Edited by: J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B-cells, plasma and/or memory cells derived from the transgenic animals. In yet another embodiment, the human binding molecules are produced by hybridomas, which are prepared by fusion of B-cells obtained from the above-described transgenic non-human mammals to immortalized cells. B-cells, plasma cells and hybridomas as obtainable from the above-described transgenic non-human mammals and human binding molecules as obtainable from the above-described transgenic non-human mammals, B-cells, plasma and/or memory cells and hybridomas are also a part of the disclosure.

In yet a further aspect, the disclosure provides compositions comprising at least a binding molecule, preferably a human monoclonal antibody, according to the disclosure, at least a functional variant thereof, at least an immunoconjugate, according to the disclosure, and/or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules of the disclosure may be coated in or on a material to protect them from the action of acids or other natural or non-natural conditions that may inactivate the binding molecules.

In yet a further aspect, the disclosure provides compositions comprising at least a nucleic acid molecule as defined in the disclosure. The compositions may comprise aqueous solutions such as aqueous solutions containing salts (e.g., NaCl or salts as described above), detergents (e.g., SDS) and/or other suitable components.

Furthermore, the disclosure pertains to pharmaceutical compositions comprising at least a binding molecule, such as a human monoclonal antibody, of the disclosure (or functional fragment or variant thereof), at least an immunoconjugate, according to the disclosure, at least a composition, according to the disclosure, or combinations thereof. The pharmaceutical composition of the disclosure further comprises at least one pharmaceutically acceptable excipient. Pharmaceutically acceptable excipients are well known to the skilled person. The pharmaceutical composition, according to the disclosure, may further comprise at least one other therapeutic agent. Suitable agents are also well known to the skilled artisan.

A monoclonal antibody product directed against a single epitope can sometimes be more sensitive to variations of the virus as compared to polyclonal antibodies. This might increase the risk of the generation of escape mutants. A combination of two monoclonal antibodies that recognize distinct epitopes could circumvent this drawback.

Therefore, in certain embodiments, the pharmaceutical composition, according to the disclosure, comprises at least one additional binding molecule, i.e., the pharmaceutical composition can be a cocktail or mixture of binding molecules. The pharmaceutical composition may comprise at least two binding molecules, according to the disclosure, or at least one binding molecule, according to the disclosure, and at least one further Hepatitis B virus binding and/or neutralizing molecule, such as another antibody directed against another epitope on the HBsAg protein or against other antigenic structures present on Hepatitis B viruses, and/or a binding molecules neutralizing one or more other pathogens. In another embodiment, the additional binding molecule may be formulated for simultaneous separate or sequential administration.

In certain embodiments, the binding molecules exhibit synergistic neutralizing activity, when used in combination. As used herein, the term “synergistic” means that the combined effects of the binding molecules when used in combination are greater than their additive effects when used individually. The synergistically acting binding molecules may bind to different structures on the same or distinct fragments of Hepatitis B virus. A way of calculating synergy is by means of the combination index. The concept of the combination index (CI) has been described by Chou and Talalay (1984). The compositions may, e.g., comprise one binding molecule having neutralizing activity and one non-neutralizing binding molecule. The non-neutralizing and neutralizing binding molecules may also act synergistically in neutralizing Hepatitis B virus.

In certain embodiments, the pharmaceutical composition may comprise at least one binding molecule, according to the disclosure, and at least one further binding molecule, preferably a further Hepatitis B virus neutralizing binding molecule. The binding molecules in the pharmaceutical composition preferably are capable of reacting with Hepatitis B viruses of different subtypes. The binding molecules may have a high binding potency and a broad specificity. Preferably, both binding molecules are cross-neutralizing molecules in that they each neutralize Hepatitis B viruses of different subtypes. In addition, preferably, they neutralize as many strains of each of the different Hepatitis B virus subtypes as possible.

In certain embodiments, the pharmaceutical composition comprises at least one other prophylactic and/or therapeutic agent. Preferably, the further therapeutic and/or prophylactic agents are agents capable of preventing and/or treating a Hepatitis B virus infection and/or a condition resulting from such an infection. Therapeutic and/or prophylactic agents include, but are not limited to, anti-viral agents. Such agents can be binding molecules, small molecules, organic or inorganic compounds, enzymes, polynucleotide sequences, anti-viral peptides, etc. These can be used in combination with the binding molecules of the disclosure. “In combination” herein means simultaneously, as separate formulations, or as one single combined formulation, or according to a sequential administration regimen as separate formulations, in any order. Agents capable of preventing and/or treating an infection with Hepatitis B virus and/or a condition resulting from such an infection that are in the experimental phase might also be used as other therapeutic and/or prophylactic agents useful in the disclosure.

The binding molecules or pharmaceutical compositions of the disclosure can be tested in suitable animal model systems prior to use in humans. Such animal model systems include, but are not limited to, mouse, ferret and monkey.

Typically, pharmaceutical compositions must be sterile and stable under the conditions of manufacture and storage. The binding molecules, immunoconjugates, or compositions of the disclosure can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, or compositions of the disclosure can be in solution and the appropriate pharmaceutically acceptable excipient can be added and/or mixed before or at the time of delivery to provide a unit dosage injectable form. Preferably, the pharmaceutically acceptable excipient used in the disclosure is suitable to high drug concentration, can maintain proper fluidity and, if necessary, can delay absorption.

The choice of the optimal route of administration of the pharmaceutical compositions will be influenced by several factors including the physicochemical properties of the active molecules within the compositions, the urgency of the clinical situation and the relationship of the plasma concentrations of the active molecules to the desired therapeutic effect. For instance, if necessary, the binding molecules of the disclosure can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is parenteral administration such as intravenous or by inhalation.

The pharmaceutical compositions of the disclosure can be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer’s solution, Hank’s solution, isotonic sodium chloride solution, oils, fatty acids, local anesthetic agents, preservatives, buffers, viscosity or solubility increasing agents, water-soluble antioxidants, oil-soluble antioxidants and metal chelating agents.

In a further aspect, the binding molecules such as human monoclonal antibodies (functional fragments and variants thereof), immunoconjugates, compositions, or pharmaceutical compositions of the disclosure can be used as a medicament or diagnostic agent. So, methods of diagnosis, treatment and/or prevention of a Hepatitis B virus infection using the binding molecules, immunoconjugates, compositions, or pharmaceutical compositions of the disclosure are another aspect of the disclosure. The above-mentioned molecules can inter alia be used in the diagnosis, prophylaxis, treatment, or combination thereof, of an infection caused by a Hepatitis B virus. They are suitable for treatment of yet untreated patients suffering from a Hepatitis B virus infection and patients who have been or are treated for a Hepatitis B virus infection. In a particular embodiment, they are suitable for preventing re-infection by Hepatitis B virus of a new liver after transplantation.

The above-mentioned molecules or compositions may be employed in conjunction with other molecules useful in diagnosis, prophylaxis and/or treatment. They can be used in vitro, ex vivo or in vivo. For instance, the binding molecules such as human monoclonal antibodies (or functional variants thereof), immunoconjugates, compositions or pharmaceutical compositions of the disclosure can be co-administered with a vaccine against Hepatitis B virus (if available). Alternatively, the vaccine may also be administered before or after administration of the molecules of the disclosure. Instead of a vaccine, anti-viral agents can also be employed in conjunction with the binding molecules of the disclosure. Suitable anti-viral agents are mentioned above.

The molecules are typically formulated in the compositions and pharmaceutical compositions of the disclosure in a therapeutically or diagnostically effective amount. Alternatively, they may be formulated and administered separately. For instance, the other molecules such as the anti-viral agents may be applied systemically, while the binding molecules of the disclosure may be applied intravenously.

Treatment may be targeted at patient groups that are exposed to Hepatitis B virus. Such patient groups include, but are not limited to, e.g., patients undergoing liver transplantation due to HBV, infants born from HBsAg positive mothers, healthcare workers exposed to blood containing HBsAg, persons exposed to HBV due to sexual and/or household contact to HBsAg positive individuals, and chronically infected patients who have been treated with an antiviral compound but have shown an inadequate antiviral response.

Dosage regimens can be adjusted to provide the optimum desired response (e.g., a therapeutic response). A suitable dosage range may, for instance, be 0.01-100 mg/kg body weight, preferably 0.1-50 mg/kg body weight, preferably 0.01-15 mg/kg body weight. Furthermore, for example, a single bolus may be administered, several divided doses may be administered over time or the dose may be proportionally reduced or increased as indicated by the exigencies of the therapeutic situation. The molecules and compositions, according to the disclosure, are preferably sterile. Methods to render these molecules and compositions sterile are well known in the art. The other molecules useful in diagnosis, prophylaxis and/or treatment can be administered in a similar dosage regimen as proposed for the binding molecules of the disclosure. If the other molecules are administered separately, they may be administered to a patient prior to (e.g., 2 min, 5 min, 10 min, 15 min, 30 min, 45 min, 60 min, 2 hrs, 4 hrs, 6 hrs, 8 hrs, 10 hrs, 12 hrs, 14 hrs, 16 hrs, 18 hrs, 20 hrs, 22 hrs, 24 hrs, 2 days, 3 days, 4 days, 5 days, 7 days, 2 weeks, 4 weeks or 6 weeks before), concomitantly with, or subsequent to (e.g., 2 min, 5 min, 10 min, 15 min, 30 min, 45 min, 60 min, 2 hrs, 4 hrs, 6 hrs, 8 hrs, 10 hrs, 12 hrs, 14 hrs, 16 hrs, 18 hrs, 20 hrs, 22 hrs, 24 hrs, 2 days, 3 days, 4 days, 5 days, 7 days, 2 weeks, 4 weeks or 6 weeks after) the administration of one or more of the human binding molecules or pharmaceutical compositions of the disclosure. The exact dosing regimen is usually sorted out during clinical trials in human patients.

Human binding molecules and pharmaceutical compositions comprising the human binding molecules are particularly useful, and often preferred, when to be administered to human beings as in vivo therapeutic agents, since recipient immune response to the administered antibody will often be substantially less than that occasioned by administration of a monoclonal murine, chimeric or humanized binding molecule.

In another aspect, the disclosure concerns the use of the binding molecules such as neutralizing human monoclonal antibodies (functional fragments and variants thereof), immunoconjugates, nucleic acid molecules, compositions or pharmaceutical compositions, according to the disclosure, in the preparation of a medicament for the diagnosis, prophylaxis, treatment, or combination thereof, of an Hepatitis B virus infection.

Next to that, kits comprising at least a binding molecule such as a neutralizing human monoclonal antibody (functional fragments and variants thereof), at least an immunoconjugate, at least a nucleic acid molecule, at least a composition, at least a pharmaceutical composition, at least a vector, at least a host, according to the disclosure, or a combination thereof, are also an aspect of the disclosure. Optionally, the above-described components of the kits of the disclosure are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about, for example, the indications, usage, dosage, manufacture, administration, contraindications and/or warnings concerning the use of such therapeutic, prophylactic or diagnostic products.

The binding molecules, according to the disclosure, can also be advantageously used as a diagnostic agent in an in vitro method for the detection of Hepatitis B virus. The disclosure, thus, further pertains to a method of detecting Hepatitis B subtype virus in a sample, wherein the method comprises the steps of:

(a) Assaying the level of Hepatitis B virus antigen in a biological sample using a binding molecule, according to the disclosure, and/or an immunoconjugate, according to the disclosure; and (b) Comparing the assayed level of Hepatitis B virus antigen with a control level whereby an increase in the assayed level of Hepatitis B virus antigen compared to the control level of the Hepatitis B virus antigen is indicative of a Hepatitis B virus infection.

The biological sample may be a biological sample including, but not limited to, blood, serum, stool, sputum, nasopharyngeal aspirates, bronchial lavages, urine, tissue or other biological material from (potentially) infected subjects, or a non-biological sample such as water, drink, etc. The (potentially) infected subjects may be human subjects, but also animals that are suspected as carriers of Hepatitis B virus might be tested for the presence of the virus using the human binding molecules or immunoconjugates of the disclosure. The sample may first be manipulated to make it more suitable for the method of detection. Manipulation means inter alia, treating the sample suspected to contain and/or containing the virus in such a way that the virus will disintegrate into antigenic components such as proteins, (poly)peptides or other antigenic fragments. Preferably, the human binding molecules or immunoconjugates of the disclosure are contacted with the sample under conditions which allow the formation of an immunological complex between the human binding molecules and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, SPR, BLI and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates of the disclosure are conveniently bonded to the inside surface of microtiter wells. The binding molecules or immunoconjugates of the disclosure may be directly bonded to the microtiter well. However, maximum binding of the binding molecules or immunoconjugates of the disclosure to the wells might be accomplished by pre-treating the wells with polylysine prior to the addition of the binding molecules or immunoconjugates of the disclosure. Furthermore, the binding molecules or immunoconjugates of the disclosure may be covalently attached by known means to the wells. Generally, the binding molecules or immunoconjugates are used in a concentration between 0.01 to 100 μg/ml for coating, although higher as well as lower amounts may also be used. Samples are then added to the wells coated with the binding molecules or immunoconjugates of the disclosure.

The disclosure further provides methods of treating or preventing a Hepatitis B virus infection in a subject, comprising administering to the subject a therapeutically or prophylactically effective amount of the binding molecules, immunoconjugates and/or pharmaceutical compositions of the disclosure. In certain embodiments, the subject is a mammal, preferably a human.

Furthermore, binding molecules of the disclosure can be used to identify specific binding structures of Hepatitis B virus. The binding structures can be epitopes on proteins and/or polypeptides. They can be linear, but also structural and/or conformational. In one embodiment, the binding structures can be analyzed by means of PEPSCAN analysis (see inter alia WO 84/03564, WO 93/09872, Slootstra et al., 1996). Alternatively, a random peptide library comprising peptides from a protein of Hepatitis B virus can be screened for peptides capable of binding to the binding molecules of the disclosure.

The disclosure is further illustrated in the following examples and figures. The examples are not intended to limit the scope of the disclosure in any way.

EXAMPLES

Example 1

Stable Conformation of the CR8097 Antibody

A panel of several antibodies has been tested for their ability to bind and neutralize different sero/genotypes of HBV. One antibody surprisingly outperformed the rest of the panel. However, this antibody displayed a heterogeneous conformation demonstrated by SEC-MALS (size exclusion chromatography-matrix assisted light scattering) analysis. FIG. 1 shows that the antibody elutes from a g3000SW$_{XL}$ column in two separate peaks that correspond to two monomeric species with similar molecular weights (thick line). In order to address this problem the antibody was mutated. As demonstrated in FIG. 1, this resulted in the production of a stable monomeric antibody preparation that eluted from the SEC column in a single homogeneous peak (thin line) with the expected MW for an IgG1, as directly measured by MALS.

Thus, the binding molecule against HBV, according to the disclosure (CR8097) has proven to be manufactured efficiently, which makes it appropriate for industrial production on large scale.

Example 2

Breadth of Binding of CR8097 as Measured by FACS

A FACS staining was performed on HEK293F cells, each transfected with a construct expressing a specific HBsAg serotype, to assess how many serotypes of HBV are recognized by mAb CR8097. The HBsAg sequences used in this study were selected from the large Japanese NIG HBV database, which contains more than 6000 HBV sequences (for link see the World Wide Web at s2as02.genes.nig.ac.jp/. The strain selection was performed by serotype classification of all HBsAg sequences in the database and subsequent calculation of the most central strain for each serotype (currently 11 serotypes have been defined) based on the extracellular loop sequence of HBsAg, which stretches from residue 100 to 207. Next, for each serotype a strain was selected closest to the most central strain (see Table 1). In this way, the most representative HBV serotypes could be selected. In addition, the genotype of each selected serotype was determined (when possible) and for two major serotypes (ayw1 and adw2), additional genotypes were selected to include as many genotypes as possible (see Table 1). In total 15 different HBsAg sequences were selected, synthesized and cloned into expression vectors.

Intracellular FACS staining was performed 48 h after transfection by fixation of the cells (15 min incubation at RT with 3% paraformaldehyde in PBS), permeabilization of the cells (30 minutes incubation at RT with 0.1% triton in PBS plus 1% BSA) followed by incubating the cells for one hour at RT with 4 μg/ml of CR8097 or an irrelevant IgG in blocking buffer (PBS with 0.1% Tween-20 and 1% BSA). Detection of CR8097 or irrelevant IgG was performed by incubating with Alexafluor 647 labeled goat-anti-human antibody (1000× diluted in blocking buffer) for one hour at RT. FACS analysis was performed on Canto II from BD Bioscience using transfected cells incubated with only secondary antibody as a negative control.

TABLE 1

Overview of selected HBV strains from which the HBsAg sequences were used for expression and binding of CR8097.

| n | Serotype | Genotype | Genbank Accession nr |
|---|---|---|---|
| 1 | adw2 | B | EU306695 |
| 2 | ayw2 | D | GU456649 |
| 3 | ayw1 | B | FJ349236 |
| 4 | adrq− | C | AY247031 |
| 5 | ayr | C | EU916237 |
| 6 | adw4q+ | A | AJ605042 |
| 7 | adrq+ | C | GQ475328 |
| 8 | ayw4 | E | EU239219 |

TABLE 1-continued

Overview of selected HBV strains from which the HBsAg sequences were used for expression and binding of CR8097.

| n | Serotype | Genotype | Genbank Accession nr |
|---|---|---|---|
| 9 | adw4q− | F | AB036905 |
| 10 | adw3 | unknown | EU487256 |
| 11 | ayw3 | D | AY796031 |
| 12 | adw2 | I | GU357844 |
| 13 | ayw1 | A | AP011088 |
| 14 | adw2 | A | GQ477466 |
| 15 | adw2 | C | EU939571 |

Figure 2:
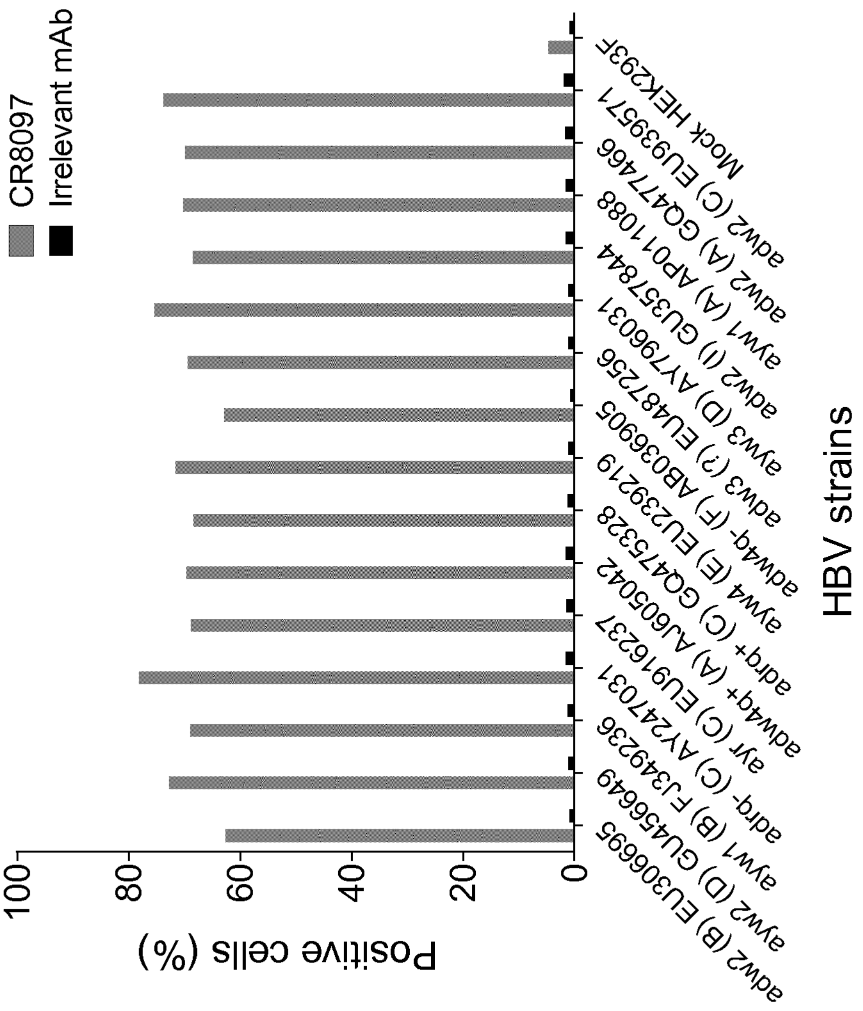
FIG. 2 Overview of intracellular FACS binding of CR8097 to HEK293F cells each transfected with an HBsAg expression construct representing major sero/genotypes of HBV. Mock HEK293F cells were transfected with a GFP expressing construct.

The binding data in FIG. 2 show that CR8097 recognizes all major subtypes of HBV, as opposed to binding molecules disclosed in the prior art in, e.g., PCT/IL97/00183 and PCT/IL97/00184, which did not recognize HBsAg subtype adw2 (genotype C), (Eren et al., 2000, Hepatology 32, 588).

Example 3

Binding of CR8097 to HBsAg Escape Mutants

Figure 3:
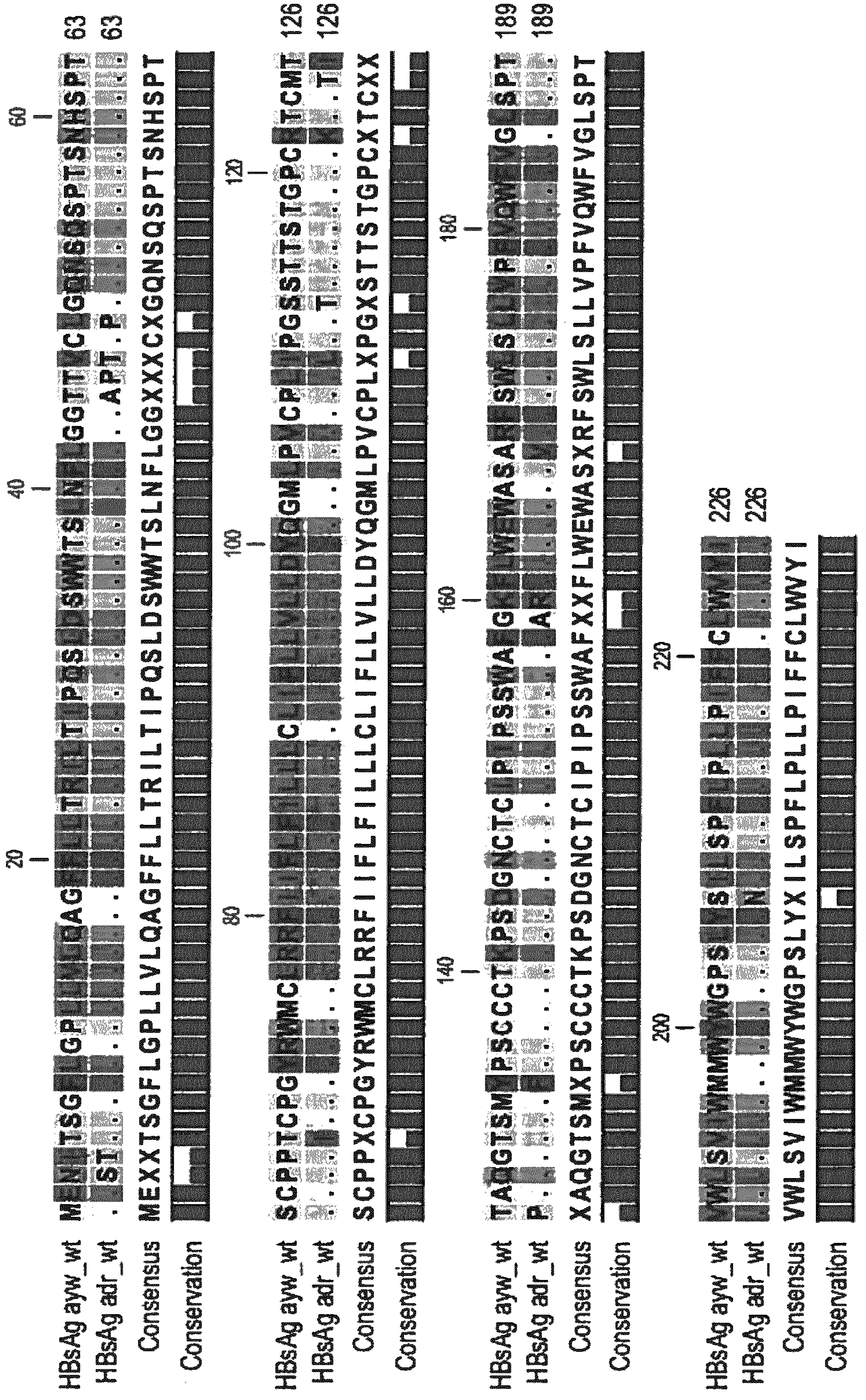
FIG. 3 Overview of the polypeptide sequence of two different subtypes of HBsAg: ayw3 (SEQ ID NO:11) and adr (SEQ ID NO:12). The consensus sequence is identical to SEQ ID NO:13.

Several options are available for the treatment or prevention of HBV infection, which are amongst others vaccination using recombinant HBsAg, immunotherapy with HBIg or treatment with polymerase inhibitors. Each of these treatments may induce mutations in the HBsAg protein and are either essential for HBV escape mechanism or these mutations are introduced as a consequence of mutations in the overlapping polymerase gene (for review see Sheldon et al. JAC (2008) p 766-768). In order to assess whether such escape mutants would affect the binding of CR8097 a panel of HBsAg mutants was recombinantly expressed in HEK293F cells followed by intracellular FACS analysis. For this analysis the most commonly observed HBsAg escape mutations (see Table 2) were selected and introduced in two different wild-type sequences of HBsAg, being ayw and adr. The wild-type sequences are shown in FIG. 3.

Intracellular FACS staining was performed 48 h after transfection by fixation of the cells (15 min incubation at RT with 3% paraformaldehyde in PBS), permeabilization of the cells (30 minutes incubation at RT with 0.1% triton in PBS plus 1% BSA) followed by incubating the cells for one hour at RT with 4 μg/ml of CR8097 or an irrelevant IgG in blocking buffer (PBS with 0.1% Tween-20 and 1% BSA). Detection of CR8097 or irrelevant IgG was performed by incubating with Alexafluor 647 labeled goat-anti-human antibody (1000× diluted in blocking buffer) for one hour at RT. FACS analysis was performed on Canto II from BD Bioscience using transfected cells incubated with only secondary antibody as a negative control (FIG. 4).

Figure 4:
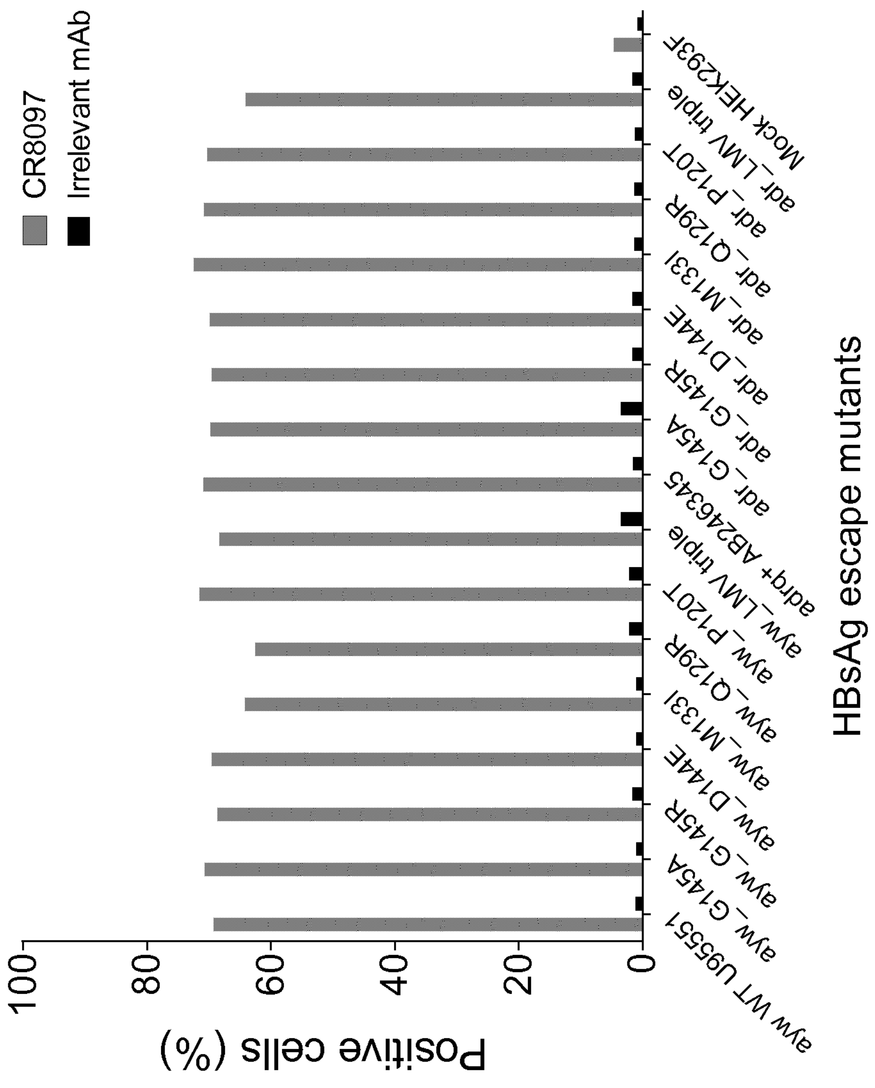
FIG. 4 Overview of intracellular FACS binding of CR8097 to HEK293F cells each transfected with an HBsAg expression construct representing commonly observed HBsAg escape mutants. Mock HEK293F cells were transfected with a GFP expressing construct.

Data show that all generated HBsAg mutants were recognized by CR8097 (FIG. 4).

TABLE 2

List of mutations introduced in HBsAg wild-type sequences

| Mutations in HBsAg | Background |
|---|---|
| P120T | Vaccine/HBIg induced |
| Q129R | Vaccine/HBIg induced |
| M133I | Vaccine/HBIg induced |
| D144R | Vaccine/HBIg induced |
| G145R | Most frequent HBIg escape mutation |
| G145A | Vaccine/HBIg induced |

TABLE 2-continued

List of mutations introduced in HBsAg wild-type sequences

| Mutations in HBsAg | Background |
|---|---|
| E164D/I195M/W196S (DMS triple mutant) | Due to gene overlap three mutations have been described in HBsAg that are actually inhibitor (nucleoside analog) induced |

Example 4

Neutralization Potency of HBV Specific IgGs as Measured by In Vitro Neutralization Assay The in vitro neutralization potency of anti-HBV monoclonal antibodies was assessed in an in vitro neutralization assay using serum from mice that have been transplanted with a human liver and subsequently infected with a hepatitis B virus of serotype adr (genotype C) and a hepatitis B virus of serotype ayw3 (genotype D). In this assay antibody dilutions were first incubated with a fixed amount of HBV containing serum, after which the virus was allowed to infect differentiated HepaRG cells (human hepatoma cell line susceptible for HBV infection), which were cultured in a 24-well plate. Eleven days after infection the infectivity was detected by measuring HBsAg expression levels using a commercial ELISA. The measured OD values were fitted using a 4-parameter fit from which the $IC_{50}$ values were calculated (note an $IC_{50}$ value represents the concentration at which 50% of neutralization is observed).

Figure 5:
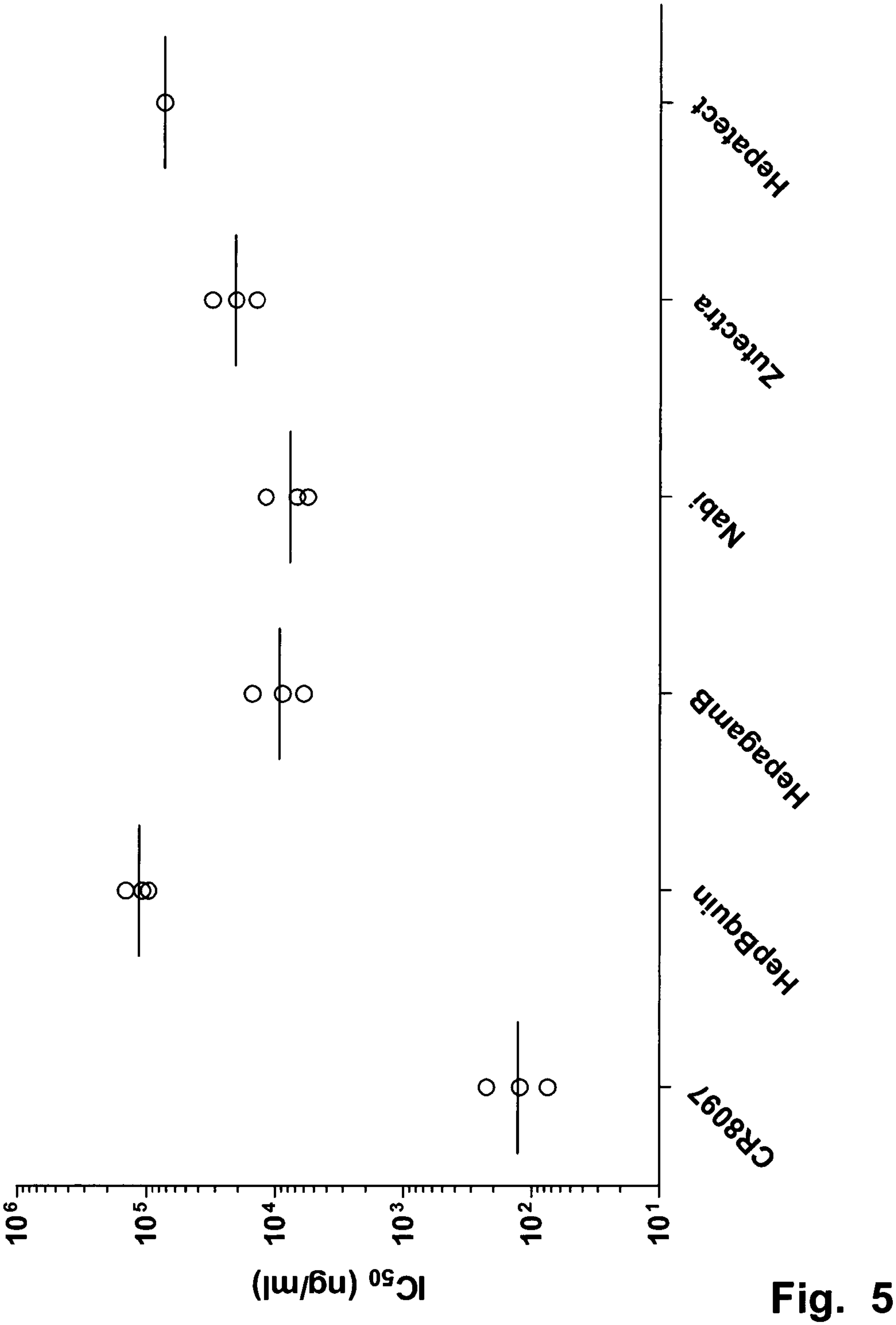
FIG. 5 In vitro neutralization potency of CR8097 on HBV genotype C, serotype adr.
Figure 6:
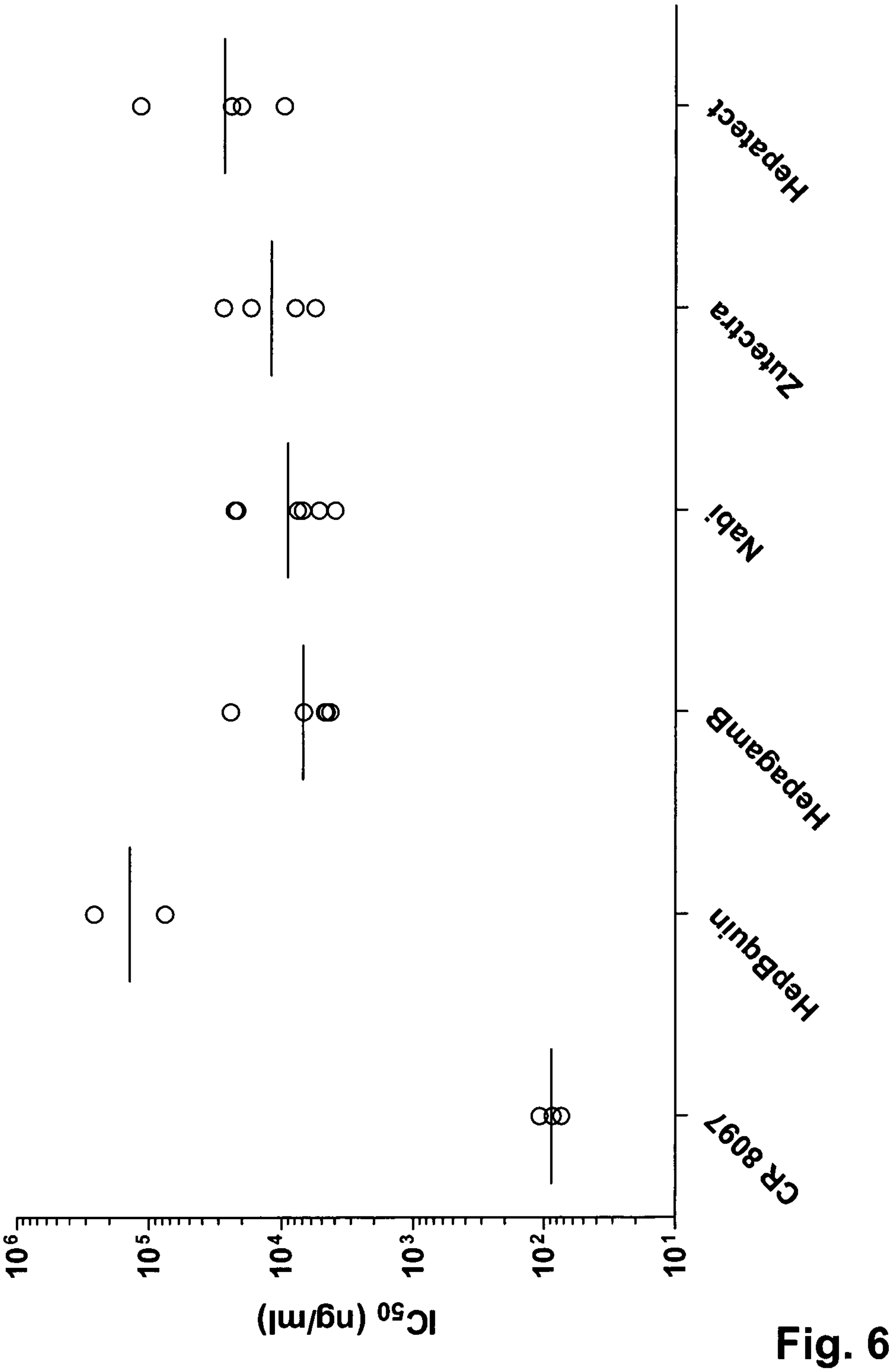
FIG. 6 In vitro neutralization potency of CR8097 on HBV genotype D, serotype ayw3.

From these data (see FIG. 5 and FIG. 6) it is clear that the potency of CR8097 is at least 100-fold higher than the tested HBIg batches.

Example 5

The in vivo efficacy of anti-HBV specific IgGs was assessed using PXB Mice®. These mice were generated by transplanting human liver cells in albumin enhancer/promoter-driven urokinase plasminogen activator transgenic/severe combined immunodeficiency disease (uPA/SCID) recipient mice followed by infection with hepatitis B virus (genotype C, serotype adr). One day before the HBV inoculation, each group of mice was dosed intravenously with IgG. At day zero mice were inoculated intravenously with $1\times10^5$ copies of HBV. Control mice were only inoculated with HBV, but did not receive IgG. Nabi-HB from Nabi was used as source of HBIg, as this HBIg shows highest in vitro neutralization potency on HBV (genotype C, serotype adr).

Figure 7:
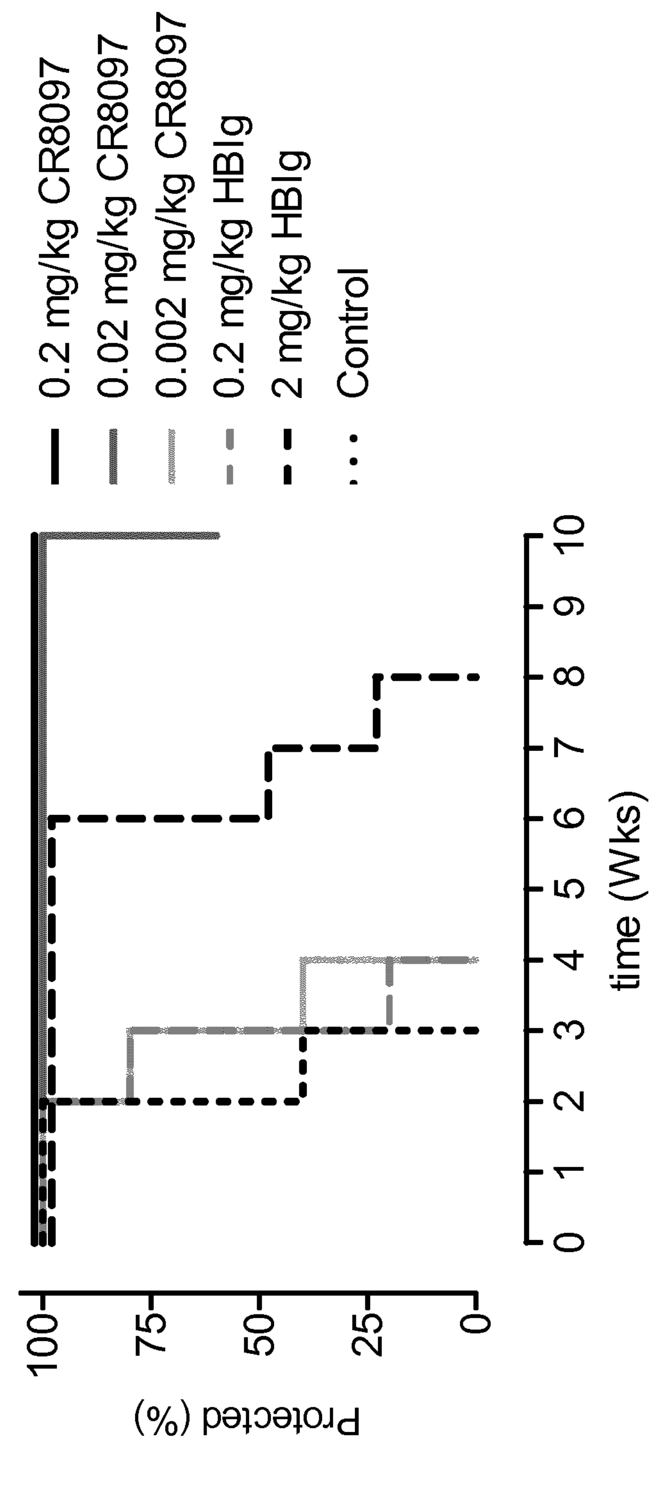
FIG. 7 Prophylactic in vivo efficacy of CR8097 on HBV genotype C, serotype adr.

HBV infection was monitored weekly by measuring HBV titers (HBV genome equivalence/ml by Q-PCR) in mouse serum. The protective effect of the IgG doses were expressed as time-to-infection calculated from Kaplan-Meijer curves. Mice were no longer protected if the HBV titers in 50% of a group were higher than the detection limit, being 4000 HBV copies/ml. In the control group, protection was only obtained for 2 weeks. When given the highest doses of CR8097 (0.2 and 0.02 mg/kg) protection was obtained for longer than 10 weeks. Protection of 0.2 mg/kg HBIg is comparable with protection of 0.002 mg/kg CR8097, being 3 weeks (see FIG. 7), which indicates that the protective efficacy of CR8097 is ~100-fold higher than HBIg.

| SEQUENCES |
| --- |
| > CR8097 VH CDR1 (SEQ ID NO: 1)<br>GFTFSNNW |
| > CR8097 VH CDR2 (SEQ ID NO: 2)<br>ISTDGMST |
| > CR8097 VH CDR3 (SEQ ID NO: 3)<br>VRGSTYYFGSGSLNF |
| > CR8097 VL CDR1 (SEQ ID NO: 4)<br>NSDIGNYDY |
| > CR8097 VL CDR2 (SEQ ID NO: 5)<br>DVS |
| > (SEQ ID NO: 6)<br>SSYAGTFTYVV |
| > CR8097 VH (SEQ ID NO: 7)<br>EVQLVESGGGLVQPGGSLRVSCEVSGFTFSNNWMHWVRQAPGKGPVWVSR<br>ISTDGMSTSYAEFVKGRFTISRDNARNTLYLQMNSLRDEDTAVYYCVRGS<br>TYYFGSGSLNFWGQGTTVIVSS |

-continued

| SEQUENCES |
| --- |
| > CR8097 VL (SEQ ID NO: 8)<br>QSALTQPRSVSGSPGQSVTISCTGTNSDIGNYDYVSWYQQHPGKAPRLII<br>YDVSERPSGVPNRFSGSKSGNTASLTISGLQAEDESDYFCSSYAGTFTYV<br>VFGGGTKLTVL |
| > CR8097 HC (SEQ ID NO: 9)<br>EVQLVESGGGLVQPGGSLRVSCEVSGFTFSNNWMHWVRQAPGKGPVWVSR<br>ISTDGMSTSYAEFVKGRFTISRDNARNTLYLQMNSLRDEDTAVYYCVRGS<br>TYYFGSGSLNFWGQGTTVIV**SS**ASTKGPSVFPLAPSSKSTSGGTAALGCL<br>VKDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPP<br>KPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPRE<br>PQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSP<br>GK |
| > CR8097 LC (SEQ ID NO: 10)<br>QSALTQPRSVSGSPGQSVTISCTGTNSDIGNYDYVSWYQQHPGKAPRLII<br>YDVSERPSGVPNRFSGSKSGNTASLTISGLQAEDESDYFCSSYAGTFTYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSCQV<br>THEGSTVEKTVAPTECS |

The invention claimed is:

1. A binding molecule comprising:

a heavy chain CDR1 comprising the peptide of SEQ ID NO:1, a heavy chain CDR2 comprising the peptide of SEQ ID NO:2, a heavy chain CDR3 comprising the peptide of SEQ ID NO:3, a light chain CDR1 comprising the peptide of SEQ ID NO:4, a light chain CDR2 comprising the peptide of SEQ ID NO:5, and a light chain CDR3 comprising the peptide of SEQ ID NO:6, which binds to an epitope on a Hepatitis B virus protein.

2. The binding molecule according to claim 1, wherein the binding molecule comprises a heavy chain variable region comprising the peptide of SEQ ID NO:7 and a light chain variable region comprising the peptide of SEQ ID NO:8.

3. The binding molecule according to claim 1, wherein the binding molecule comprises a heavy chain comprising the peptide of SEQ ID NO:9 and a light chain comprising the peptide of SEQ ID NO:10.

4. The binding molecule of claim 1, wherein the binding molecule neutralizes a Hepatitis B virus in an in vitro assay.

5. The binding molecule of claim 1, wherein the binding molecule is a human monoclonal antibody, or an antigen-binding fragment thereof.

6. An immunoconjugate, comprising:

at least one binding molecule of claim 1, and at least one tag.

7. A nucleic acid molecule encoding a binding molecule comprising:

a heavy chain CDR1 comprising the peptide of SEQ ID NO:1, a heavy chain CDR2 comprising the peptide of SEQ ID NO:2, a heavy chain CDR3 comprising the peptide of SEQ ID NO:3, a light chain CDR1 comprising the peptide of SEQ ID NO:4, a light chain CDR2 comprising the peptide of SEQ ID NO:5, and a light chain CDR3 comprising the peptide of SEQ ID NO:6.

8. A method of treating a subject for hepatitis B virus infection, the method comprising: administering to a subject the binding molecule of claim 1 in the treatment of a Hepatitis B infection caused by a Hepatitis B virus.

9. A pharmaceutical composition comprising:

the binding molecule of claim 1, and a pharmaceutically acceptable carrier or excipient.

10. The pharmaceutical composition according to claim 9, further comprising:

a Hepatitis B neutralizing binding molecule.

11. A method of detecting a Hepatitis B virus infection, the method comprising: (a) assaying the level of Hepatitis B virus antigen in a biological sample utilizing the binding molecule of claim 1; and (b) comparing the assayed level of Hepatitis B virus antigen with a control level whereby an increase in the assayed level of Hepatitis B virus antigen compared to the control level of the Hepatitis B virus antigen is indicative of a Hepatitis B virus infection.

12. A humanized, chimeric, or human monoclonal antibody or antibody fragment that binds to hepatitis B virus (HBV) surface antigen and neutralizes at least one HBV genotype, the antibody comprising:

a heavy chain CDR1 comprising the peptide of SEQ ID NO:1, a heavy chain CDR2 comprising the peptide of SEQ ID NO:2, a heavy chain CDR3 comprising the peptide of SEQ ID NO:3, a light chain CDR1 comprising the peptide of SEQ ID NO:4, a light chain CDR2 comprising the peptide of SEQ ID NO:5, and a light chain CDR3 comprising the peptide of SEQ ID NO:6.

13. The antibody or antibody fragment of claim 12, wherein a heavy chain variable region comprises the peptide of SEQ ID NO:7 and a light chain variable region comprises the peptide of SEQ ID NO:8.

14. The antibody or antibody fragment of claim 12, wherein a heavy chain comprises the peptide of SEQ ID NO:9 and the light chain comprises the peptide of SEQ ID NO:10.

* * * * *

UNITED STATES PATENT AND TRADEMARK OFFICE
CERTIFICATE OF CORRECTION

PATENT NO. : 9,512,201 B2
APPLICATION NO. : 14/428904
DATED : December 6, 2016
INVENTOR(S) : Ingrid van den Nieuwenhof et al.

It is certified that error appears in the above-identified patent and that said Letters Patent is hereby corrected as shown below:

In the Specification
Column 11, Line 50, change "F(ab′), F(ab)$_2$, Fv" to -- F(ab′), F(ab′)$_2$, Fv --

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*